United States Patent [19]

Tuominen et al.

[11] Patent Number: 4,886,888

[45] Date of Patent: Dec. 12, 1989

[54] EXTRACTION OF AMINO AN ACID FROM AQUEOUS MIXTURES THEREOF

[75] Inventors: Francis W. Tuominen, Minneapolis; Ronald R. Swanson, Taylors Falls; Phillip L. Mattison, New Brighton; Kenneth D. MacKay, Plymouth; Bradley W. Glorvigen, St. Paul, all of Minn.

[73] Assignee: Henkel Corporation, Ambler, Pa.

[21] Appl. No.: 945,735

[22] Filed: Dec. 22, 1986

Related U.S. Application Data

[62] Division of Ser. No. 617,767, Jun. 6, 1984, Pat. No. 4,661,606.

[51] Int. Cl.$^4$ .................. C07D 209/20; C07D 99/12; C07D 101/02

[52] U.S. Cl. .................. 548/497; 562/433; 562/443; 562/445; 562/448; 562/553; 562/554; 562/559; 562/523; 562/562; 562/563; 562/570; 562/576

[58] Field of Search .............. 562/443, 448, 554, 559, 562/562, 563, 570, 523, 576, 443; 548/467, 497

[56] References Cited

U.S. PATENT DOCUMENTS

2,681,927 6/1954 McCollum et al. .................. 562/443
3,318,867 5/1967 Jahnke .................. 260/210

FOREIGN PATENT DOCUMENTS

58-57158 12/1983 Japan .
59-23797 6/1984 Japan .

OTHER PUBLICATIONS

Acta Pharm Suec. 12, 407-416 (1975); Quantitative Determinations by Ion Pair Extraction, Part 12. Extraction of Amino Acids With Quaternary Ammonium Ions, Nordgren and Modin.

Primary Examiner—David B. Springer
Attorney, Agent, or Firm—Ernest G. Szoke; Wayne C. Jaeschke; Patrick J. Span

[57] ABSTRACT

Amino acids can be purpified and/or concentrated by extracting aqueous mixtures such as fermentation broths by contacting an aqueous mixture containing amino acids with an organic solution containing a water insoluble extractant selected from the group consisting of:

1. A quaternary ammonium ion having the formula:

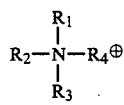

where $R_1$, $R_2$, $R_3$ and $R_4$ are aliphatic, each having from 1 to 22 carbon atoms, and together have a minimum of 25 carbon atoms, and where at least three of the four R groups are at least a $C_4$.

2. A quaternary phosphonium ion having the formula:

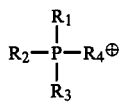

where $R_1$, $R_2$, $R_3$ and $R_4$ are as defined above.

3. A tertiary sulfonium ion having the formula:

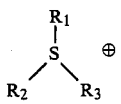

where $R_1$, $R_2$ and $R_3$ each are aliphatic with from 1 to 22 carbon atoms, and together have a minimum of 24 carbons and where at least two of these groups are at least a $C_6$.

4. An organic boride ion having the formula:

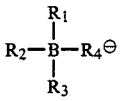

where $R_1$, $R_2$, $R_3$ and $R_4$ are as previously defined.

5. An organic sulfonic acid selected from the group consisting of:
Organic sulfonic acids having the structural formula:

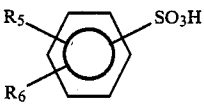

where $R_5$ and $R_6$ are aliphatic hydrocarbon groups individually with from about 6 to about 22 carbon atoms, where $R_5$ and $R_6$ together contain at least 18 carbon atoms, and where neither $R_5$ nor $R_6$ are smaller than a $C_6$; and organic sulfonic acids having the structural formula;

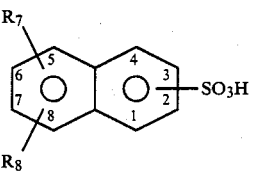

where $R_7$ and $R_8$ are aliphatic hydrocabon groups containing from about 4 to about 22 carbon atoms, where $R_7$, $R_8$, or the sulfonic group may be attached to positions 1–8 on the aromatic rings, and where neither $R_7$ nor $R_8$ is smaller than a $C_4$, and where $R_7$ and $R_8$ together have at least 18 carbon atoms.

8 Claims, No Drawings

EXTRACTION OF AMINO AN ACID FROM AQUEOUS MIXTURES THEREOF

This application is a division of application Ser. No. 617,767, filed June 6, 1984, U.S. Pat. 4,661,606.

BACKGROUND OF THE INVENTION

Amino acids, essential to animal and human nutrition are important as food additives, feed supplements, artificial sweeteners, and intravenous solutions; thus production and purification of amino acids is an important procedure. Descriptively, amino acids are organic acids containing an amino group. These compounds can be obtained by hydrolysis of a protein, by organic synthesis, or by fermentation. As a general rule, all naturally occurring amino acids are alpha-amino acids, having the —$NH_2$ group attached to the carbon atom next to the COOH group, beta-alanine being an exception to this generalization. Some amino acids are termed essential meaning that they are required for an organism's growth, but can not be synthesized by its body. Essential amino acids for human beings are: arginine, histidine, isoleucine, leucine, lysine, methionine, phenylalanine, threonine, tryptophan, and valine.

Due to present industrial procedures it is necessary to remove amino acids from dilute fermentation broths and other aqueous mixtures. Current methods used to remove and purify amino acids are crystallization, chromatography, ion-exchange, and extraction. One such method, described in U.S. Patent No. 2,894,954 teaches that amino acids can be removed as a solute in N-hexylamine by a plurality of liquid/liquid contacting zones. In accordance with this method the N-hexylamine is then separated from the amino acids.

Another extraction method used to separate amino acids from fermentation broths and other aqueous mixtures is discussed in: "*Quantitative determinations by ion pair extraction*", ACLA PHARM. SNEC. 12, 407–416 (1975), by Thomas Nordgren, and Rolf Modine which teaches the extraction of amino acids from fermentation broths by combining a *water soluble* extractant, tetrapentylammoniumiodide with an aqueous phase containing amino acids, and subsequently washing with methylene chloride. This method, disadvantageously has a tendency to leave water soluble ion pairs formed by the combination of extractant and amino acid in the aqueous phase, which are not extracted in the organic phase.

Another problem encountered in the purification of amino acids is how to deal with the large amounts of water involved. The problem becomes more acute when the aqueous solution is very dilute. The process of the instant invention provides an effective method of extracting amino acids from such dilute solutions. It is also an object of the instant invention to provide a process for extracting amino acids from fermentation broths and other aqueous mixtures which also, advantageously, works well at pH extremes. Other objects will become apparent as this description proceeds.

BRIEF DESCRIPTION

Amino acids can be extracted from aqueous solutions by a process comprising contacting an aqueous mixture containing amino acids with a water immiscible organic solution containing a water insoluble extractant, thereby forming two phases and separating the two phases after amino acids have transferred into the organic phase.

Amino acids to which this invention relates, can be defined as an organic acid containing an amino group. Most naturally occurring acids in this category are alpha-amino acids having the —$NH_2$ group attached to the carbon atom next to the COOH group; beta-alanine being a naturally occurring amino acid not following this rule.

Water insoluble extractants used to draw amino acids into organic solutions are selected from the group consisting of:

1. A quaternary ammonium ion having the formula:

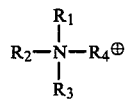

$R_1$, $R_2$, $R_3$, and $R_4$ individually are aliphatic hydrocarbon groups containing from about 1 to about 22 carbon atoms and where $R_1$, $R_2$, $R_3$ and $R_4$ together have a minimum of 25 carbon atoms, and were at least three of the four R groups are at least a $C_4$;

2. A quaternary phosphonium ion having the formula:

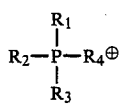

where $R_1$, $R_2$, $R_3$ and $R_4$ are as defined above;

3. A tertiary sulfonium ion having the formula:

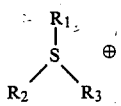

where $R_1$, $R_2$ and $R_3$ are aliphatic as defined previously, (with from 1 to 22 carbon atoms), where $R_1$, $R_2$, and $R_3$ together have a minimum of 24 carbons and where at least two of these groups are at least a $C_6$;

4. An organic boride ion having the formula:

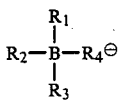

where $R_1$, $R_2$, $R_3$ and $R_4$ are aliphatic as defined previously and together have a minimum of 25 carbons and where at least 3 of these 4 groups are at least a $C_4$;

5. An organic sulfonic acid selected from the group consisting of organic sulfonic acids having the formula:

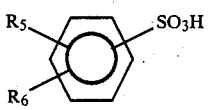

where $R_5$ and $R_6$ are aliphatic hydrocarbon groups individually having from about 6 to about 22 carbon atoms where $R_5$ and $R_6$ together contain at least 18 carbon atoms, and organic sulfonic acids having the structural formula:

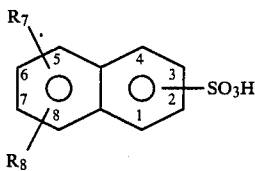

where $R_7$ and $R_8$ are aliphatic hydrocarbon groups containing from about 4 to about 22 carbon atoms; where $R_7$, $R_8$, or the sulfonic group may be attached to positions 1–8 on the aromatic rings, and where $R_7$ and $R_8$ together have at least 18 carbon atoms.

The aqueous mixture contains at least one amino acid not in its zwitterion form. Contact of the aqueous solution with the organic extractant containing solution takes place for a sufficient length of time to allow amino acids to be extracted into the organic solution. After the amino acids have transferred to the organic phase, the two phases are separated.

These extractants are not only essentially water insoluble, but are soluble in non-polar water immiscible organic phases, and are also charged ionically when dissolved. When these extractants are dissolved in the non-polar phase, amino acids are extracted from the immiscible aqueous (polar) phase that it is contacted with.

In order to be extracted in accordance with the process of the instant invention, the amino acid being removed from the aqueous mixture must not be in its zwitterion form. This zwitterion is that form of an amino acid where the amino acid molecule contains both a positive and negative charge. This form, which will vary slightly with the specific amino acid in solution, occurs in an aqueous solution over the more neutral pH ranges (from about 4.5 to 7.5). To extract amino acids therefore, the instant invention generally requires the aqueous mixture containing amino acids to have an acidic pH value of about 4.5 or less, or a basic pH value of about 7.5 or more so that the amino acids are predominately not zwitterions. Alternatively stated, the amino acids must be in an aqueous (polar) phase having a pH such that the amino acids are either cationic or anionic. The extractants generally are oppositely charged relative to the amino acids to be extracted. Thus, for example, when water insoluble quaternary ammonium salts are used as the extractant in the organic phase, the aqueous phase must have a pH of 7.5 or greater, unless a limited and selective extraction of the more hydrophobic amino acids, such as tryptophan, phenylalanine, leucine and valine is desired, in which case the pH of the aqueous mixture can be 3 or less, so that moderate concentrations of such amino acids will extract. For a non-selective extraction of amino acids (both hydrophobic and hydrophilic amino acids) when using a cationic extractant such as a tertiary sulfonium, a quaternary phosphonic, or a quaternary ammonium salt, the pH of the aqueous phase must be basic, maintained at 7.5 or greater, in order to have a suitable extraction. When using organic sulfonic acids or organic boride extractants, the amino acids should be in an acidic aqueous phase, acceptably having a pH less than 4.5; preferably less than 3.0.

Suitably, the organic phase can be made up of one or more water immiscible (non-polar) organic solvents. Virtually any substantially water immiscible organic solvent or combination of solvents that is capable of dissolving the selected water immiscible extractant is suitable. Modifiers, such as alcohols, can be added to the solution to improve the extraction of the more polar amino acids, to improve phase separation and/or to improve the solubility of the extracted amino acid complex in the organic phase.

After the organic phase has extracted the amino acids from the aqueous mixture, the two phases are separated by any convenient method, and further purification and isolation of the particular amino acids can be accomplished.

An important aspect of the instant invention is the compositions of matter formed when the aqueous mixture of amino acids contacts the organic solution the previously-named extractants. Such compositions comprise: amino acid salts of the extractants selected from the group consisting of:

1. A quaternary ammonium ion having the formula:

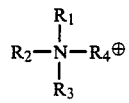

$R_1$, $R_2$, $R_3$, and $R_4$ individually are aliphatic hydrocarbon groups containing from about 1 to about 22 carbon atoms and where $R_1$, $R_2$, $R_3$ and $R_4$ together have a minimum of 25 carbon atoms, and where at least three of the four R groups are at least A $C_4$;

2. A quaternary phosphonium ion having the formula:

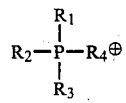

where $R_1$, $R_2$, $R_3$ and $R_4$ are as defined above, (individually are aliphatic hydrocarbon groups containing from about 1 to about 22 carbon atoms, and where $R_1$, $R_2$, $R_3$ and $R_4$ together have a minimum of 25 carbon atoms, and where at least three of the four groups are at least a $C_4$);

3. A tertiary sulfonium ion having the formula:

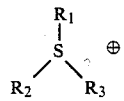

where $R_1$, $R_2$ and $R_3$ are aliphatic hydrocarbon groups containing from about 1 to about 22 carbon atoms, and where $R_1$, $R_2$, and $R_3$ together have a minimum of 24 carbons and where at least two of these groups are at least a $C_6$;

4. An organic boride ion having the formula:

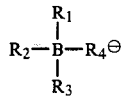

where $R_1$, $R_2$, $R_3$ and $R_4$ are aliphatic as defined previously and together have a minimum of 25 carbons and where at least 3 of these 4 groups are at least a $C_4$;

5. An organic sulfonic acid selected from the group consisting of organic sulfonic acids having the formula:

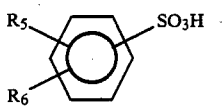

where $R_5$ and $R_6$ are aliphatic hydrocarbon groups individually having from about 6 to about 22 carbon atoms where $R_5$ and $R_6$ together contain at least 18 carbon atoms, and organic sulfonic acids having the structural formula:

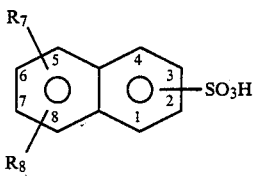

where $R_7$ and $R_8$ are aliphatic hydrocarbon groups containing from about 4 to about 22 carbon atoms; where $R_7$, $R_8$, or the sulfonic group may be attached to positions 1-8 on the aromatic rings, and where $R_7$ and $R_8$ together have at least 18 carbon atoms.

DETAILED DESCRIPTION

In order to extract amino acids from the aqueous solution or fermentation broth, the pH of this aqueous mixture is controlled so that the amino acids to be removed are not present as zwitterions. Acid or base can be added to the aqueous mixture in order to maintain the pH at the right level. Suitable acids to be used for pH control in the aqueous mixture are mineral acids, and suitable bases to be used are alkali and alkali earth metal hydroxide and ammonium hydroxide bases. The stronger acids and bases which tend to be soluble in water and insoluble in the organic phase are preferred; such acids are hydrochloric, hydrofluoric, nitric, sulfuric, hydrobromic and phosphoric. Phosphoric acid is good acidifying agent for the aqueous phase. Suitable bases for pH control in the aqueous phase include: potassium hydroxide, sodium hydroxide, ammonium hydroxide and sodium carbonate.

The concentration of the extractant used in the organic phase should be sufficient to extract a portion of the amino acids from the aqueous phase. Where a variety of amino acids are present, it is possible to limit the concentration of the extractant so that the extractant to amino acid molar concentration ratio is from about 0.25:1 to about 1.35:1. This will enable amounts of the more hydrophobic amino acid to extract and separate from the more hydrophilic amino acids.

General extractions of overall amino acids from fermentation broths and other aqueous mixtures can also be accomplished using the instant invention. In this instance an overall and substantially complete removal of amino acids from the aqueous mixture is desired. Acceptably, the ratio of extractant concentration to amino acid concentration is 1:1 on a molar basis. Preferably, the ratio should be from about 1.2 moles of extractant per amino acid molar concentration, to about 10 moles of extractant per total moles of amino acid. As previously indicated, however, the concentration of extractant can be limited to less than 1 mole per mole of amino acids in order to extract more preferentially one amino acid over another. Thus, the ratio of the number of moles of extractant in the organic solution to the number of moles of amino acids in the aqueous solution can acceptably be in the range of from about 0.25 moles of extractant per mole of amino acid to about 10 moles of extractant per mole of amino acid.

In the extraction process of the instant invention the respective concentrations of the organic and aqueous phases can vary widely depending on individual circumstances and needs. The process of the instant invention operates well with very dilute solutions.

There is no upper limit to the amount of amino acids in the aqueous phase. In fact solid or precipitated amino acids can also be in contact with the aqueous phase to permit continued replenishment of the amino acid concentration. There is no minimum concentration necessary for the amino acids in the aqueous solution. One advantage of the instant invention is that extractions can be done with very dilute solutions, in which amino acids frequently are found. For extremely dilute amino acid solutions, extractant concentrations and the organic to aqueous phase ratio can be varied to improve extraction. A solution having any detectable amount of amino acids can be extracted. The instant invention can be used to extract amino acids from solutions with amino acid concentrations as low as 10 ppm (parts per million).

The respective volumes of the phases are generally determined by individual need, such as the type of extraction system used, and the respective concentrations of the solutions. Since amino acids must frequently be extracted from very dilute aqueous solutions, the organic to aqueous volume ratio can acceptably vary from about 1:20 to about 20:1. More desirably, a more effective range for the ratio of the organic phase volume to the aqueous phase volume is from about 1:5 (organic to aqueous) to about 5:1 (organic to aqueous). A more preferred ratio for the organic phase volume to the aqueous phase volume, especially in commercial extraction systems is from about 1:3 to about 3:1.

The organic extractant phase should contact the aqueous amino acid phase for a sufficient length of time to permit the amino acids to enter the organic phase. The time of contact depends on the particular system, the type of equipment used, and upon individual needs and desires. As a general rule, however, the contact time between the organic extractant solution and the aqueous amino acid mixture should be in excess of 0.1 seconds with some equipment, but generally less than 3 hours. Naturally a minimum contact time is desired, thus a more desirable phase contact time would be in the range of from about 5 seconds to one hour while a more preferred contact time is from about 5 seconds to about 10 minutes.

After the amino acids have been extracted into the organic phase, the two phases may be separated by an convenient means for a liquid/liquid phase separation. Representative but non-exhaustive examples of means for achieving phase separations are: gravity settlers and centrifuges. Generally, any system used to separate different liquid phases can be used.

Any substantially water immiscible liquid solvent can be used in the process of the instant invention. Typically, this includes aliphatic and aromatic hydrocarbons. Aliphatic hydrocarbons such as alkanes, including cycloalkanes and halogenated alkanes are suitable; preferred alkanes have a minimum of five carbon atoms;

preferred halogenated alkanes have a minimum of two carbon atoms; aromatic hydrocarbons which can be used include benzene, and substituted products such as toluenes, xylenes and cumene. Also suitable as a solvent are those esters, ethers, ketones, and alcohols which are substantially water immiscible. Furthermore any blend of these substances or a water immiscible kerosene is also suitable.

Modifiers can be added to the solvent in addition to the extractant in order to modify or improve the extraction of amino acids. Substances, which are preferred as modifiers are alcohols in the range of from about 10 to about 13 carbon atoms and phenols such as the alkyl (8–12 carbon atom) substituted phenols, can be added to improve amino acid extraction, phase separation and/or other important characteristics of the organic solution.

After the amino acids have been extracted into the organic phase they can be further purified and isolated. Separation of the amino acids from the extractants will free the extractants for re-use in which more amino acids are extracted from other aqueous mixtures. The amino acids can be released from the extractant phase and removed from the extractant (a) by forming an amino acid precipitate by adding a gaseous salt-forming reagent such as ammonia, carbon dioxide, hydrogen chloride, hydrogen bromide, and $SO_2$ to the organic layer, or (b) by a stripping step which releases the amino acids into another acidic or basic aqueous or polar solution where they can be further purified or isolated by such procedures as precipitation, chromatography, or treatment by ion-exchange resins, or in accordance with the instant invention. The instant invention includes either (a) a stripping or (b) a precipitation step which results in the extractant regeneration and also in either a more pure, concentrated amino acid solution or in the precipitation of solid amino acids.

In the precipitation step, the organic solution holding the extractant and amino acids extracted is contacted with the gaseous salt forming substance such as gaseous $NH_3$, $CO_2$, $SO_2$, HCl, and HBr. When gas is added atmospheric or elevated pressures can be used. This gaseous addition will cause either the transformation of the amino acid from an extractable form into an unextractable form, thereby releasing it from the organic phase, or it will displace the amino acid from its salt in the organic phase as a precipitate. Whether an acidic or basic gas is used will depend upon the type of extractant used. If the extractant is anionic, such as a sulfonic acid, then the salt forming gas used may be $NH_3$, HCl or HBr. When the gas is strongly acidic gas, such as HCl or BHr, then the extractant is converted to the hydrogen form, and the amino acid precipitates from the organic phase as the acid salt, such as the hydrochloride salt. When the gas is basic, such as ammonia, then the extractant is converted to the ammonium salt, and the amino acid precipitates in the neutral zwitterionic form. If the extractant is cationic, however, such as a quaternary ammonium, quaternary phosphonium, or tertiary sulfonium salt; a gas forming substance which is ordinarily acidic in water should be used. Representative but non-exhaustive examples of these are $SO_2$, $CO_2$, HCl and HBr. For examples, when $CO_2$ is used, the extractant is converted to its carbonate or bicarbonate form, and the amino acid is precipitated in the zwitterionic form. When a strongly acidic gas such as HCl is used, the reagent is converted to the corresponding salt, such as chloride, and the amino acid is precipitated either in the zwitterionic form or as the acid salt, such as the hydrochloride salt.

Either acidic or basic aqueous stripping phase can be used to remove the amino acids from the organic solution thereby regenerating the extractant in the organic solution so that it can be reused by contact with another aqueous solution. Any aqueous acid or base can be used. Suitable acids include mineral acids such as phosphoric, $HNO_3$, $H_2SO_4$, HCl, HF, or HBr. Suitable bases are those formed from the alkali or alkali earth metals such as NaOH, KOH, $Na_2CO_3$, etc. Also suitable is ammonium hydroxide. After removing the amino acids from the organic phase they can be further purified by any previously mentioned method. Whether an acidic or basic aqueous stripping phase is used will depend on the type of extractant, the form of the amino acid desired, and the over-all system used. If the extractant is anionic, such as sulfonic acid or an organic boride, the aqueous stripping phase is maintained at a pH of less than 0.5 or greater than 2.5 when contacting the organic phase. Any of the previously named acids or bases can be used in the aqueous stripping base to achieve these pH values. If the stripping phase is strongly acidic with, for example, hydrochloric acid, the extractant is converted to the hydrogen form, and the amino acid is transferred to the aqueous phase as the acid salt, such as the hydrochloride. If the stripping phase has a pH of 2.5 or greater, as would be maintained, for example with ammonium hydroxide, the extractant is converted to its salt form, such as the ammonium salt, and the amino acid is transferred to the aqueous phase as the zwitterionic form. If, on the other hand, the extractant is cationic, as with a tertiary sulfonium, quaternary phosphonium, or quaternary ammonium ions, the aqueous stripping phase is acidified with an acid, such as hydrochloric acid or acceptably any of the previously named acids; in this case, the extractant is converted to a salt form such as the chloride, and the amino acid is transferred to the aqueous phase in either its zwitterionic form or, for example, its hydrochloride form. The extractant in the organic solution can then be reused.

The ratio of the organic to aqueous phase volumes used in the stripping step is generally greater than one, to obtain a concentration effect. The actual ratio may vary over wide limits as determined by individual need, such as the type of over-all extraction systems used, and the concentrations of the solutions. The organic to aqueous volume ratio can acceptably vary from about 1:20 to about 20:1. More desirably, a more effective range for the ratio of the organic phase volume to the aqueous phase volume is from about 1:5 (organic to aqueous) to about 5:1 (organic to aqueous). A more preferred ratio for the organic phase volume to the aqueous phase volume, especially in commercial extraction systems is from about 1:3 to about 3:1.

The temperatures and pressures used in conjunction with the steps of the instant invention should be sufficient to maintain the organic and aqueous phases as liquid. Within this limitation, any particular temperature or pressure required by any particular apparatus or phase separation system is acceptable as long as there is no decomposition of the extractants or amino acids.

In accordance with the instant invention, by using the described process, an extraction of amino acids can be made, so that a wide variety of amino acids are collected in large amounts in an organic phase. After this, instead of using the previously described stripping step, the amino acids can be purified by methods such as chromatography, precipitation, crystallization or electrophoresis. If desired, however, the instant invention can be applied in sequential extractive steps; and the conditions of each step can be arranged so that certain amino acids are encouraged to extract preferentially into a specific organic phase. For example, by using any cationic extractant of the instant invention (quaternary ammonium, quaternary phosphonium or the tertiary sulfonium salts) and by maintaining the pH of the aqueous phase in excess of 9, and/or by keeping the over-all molar ration of extractant to amino acids in the range of from about 0.25 to 3, the more hydrophobic amino acids such as: phenylalanine, tryptophan, valine and leucine, are encouraged to extract preferentially over the more hydrophilic amino acids such as lysine, glutamic acid, alanine or tyrosine. After one or more of these extractions the aqueous phase can then be acidified to lower the pH below 4.5, and then a second extraction of the acidified aqueous phase with a water-insoluble organic boride or organic sulfonic acid in a water insoluble organic solvent to remove the more hydrophilic amino acids. Thereafter, both organic phases can be stripped of the amino acids and their extractants re-used while the amino acid is then subjected to further purification.

Another sequence also possible is to extract all amino acids possible from their aqueous solutions, using a large extractant molar concentration (such as from about 1.5 moles of extractant per mole of amino acid to 20 moles of extractant per mole of amino acid) in an immiscible organic solvent. The preferred extractants are the previously named water insoluble organic sulfonic acids, or organic borides, although any of the extractants are suitable. This initial step removes amino acids from other contaminants, impurities caused by the fermentation or synthetic process, makes subsequent purification/concentration easier. After this initial extraction of all amino acids possible from their aqueous mixture, the organic phase containing these amino acids is stripped using any method previously indicated. If the amino acids are thereby transferred into an aqueous solution, selective extractions in accordance with the instant invention can be used. Such extractions would be extractions of the more hydrophobic amino acids by using limited concentrations of cationic extractants such as the quaternary ammonium or quaternary phosphonics or tertiary sulfoniums salts. After this second extraction is completed, the aqueous solution can then be contacted with a third organic phase containing any of the extractants contemplated by the instant invention. Preferred extractants for this step would be selected from any of the extractants previously indicated (the tertiary sulfoniums, organic borides, quaternary ammoniums, or organic sulfonic acids, previously shown). In this manner, by varying extractant type and concentration, and by using aqueous stripping stages, and varying the sequence of steps, amino acids such as phenylalanine can be separated from other similar acids.

Another variation which can be used to alter the selectivity of amino acid extractants in accordance with the instant invention is to use sequential extractions where one of the extractants is a quaternary ammonium salt in an organic phase which is then contacted with an aqueous mixture of amino acid maintained at pH's less than 3. Such a step would tend to extract amino acids such as phenylalanine, valine and tryptophan which are amino acids more easily extracted from aqueous phases. Other more hydrophilic amino acids would be left in the aqueous phase. Such a process would leave amino acids such as lysine, glutamic, alanine and tyrosine in the aqueous which could then be removed by more acidic extractants previously indicated such as any of the organic borides or organic sulfonic acids. Advantageously, this procedure would not require an acidification of the aqueous phase in-between the two extraction steps. In such a case the initial organic phase could have the quaternary ammonium salt concentrations range in a molar ratio of extractant to amino acid of from about 1:1 to about 20:1. Preferred concentrations of the extractant in the organic phase would depend on the hydrophobic amino acid concentration in the aqueous phase. These and other sequential variations are possible.

The following examples are offered to illustrate the invention and not to limit it. All parts and percentages are by weight unless otherwise specified.

EXAMPLE I

In this example there was employed as the extractant a quaternary ammonium salt which is commercially available and sold an ALIQIAT ® 336 by Henkel Inc. This quaternary compound is a trifatty, monomethyl quaternary ammonium chloride in which the fatty groups are derived from a mixture of the $C_8$ and $C_{10}$ straight chain alkyl groups. The compound may also be represented by the formula:

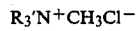

$$R_3'N^+CH_3Cl^-$$

where R' is a mixture of aliphatic hydrocarbon groups having 8-10 carbon atoms. The extractant was mixed into a solution that was 10% 1-octanol, and 90% toluene. The concentration of the quaternary ammonium salt extractant was 0.11 moles per liter. A volume of 15 milliliters (ml) of this organic solution, as the organic phase was shaken for one minute with eight aqueous solutions each having a volume of 15 ml. Each of the following amino acids was individually present in a 0.06 molar concentration: alanine, glutamic, leucine, lysine, methionine, phenylalanine, tryptophan, tyrosine. After extraction, the pH of the aqueous solution was measured at 11.5.

The aqueous solution was separated from the organic phase, and the amino acid concentration in the aqueous phase was measured; the results were:

| AMINO ACID | PERCENT EXTRACTED INTO THE ORGANIC PHASE |
|---|---|
| Alanine | 17 |
| Glutamic | 11 |
| Leucine | 40 |
| Lysine | 4 |
| Methionine | 36 |
| Phenylalanine | 60 |
| Tryptophan | 71 |
| Tyrosine | 21 |

EXAMPLE II

Extractions of six aqueous phases were completed at six different acidic pH values. The aqueous phase in each case contained 0.0005 moles of valine, was acidified with HCl, and was 15 ml in volume.

Each extracting organic phase used was 10 ml in volume. The organic solvent was ethylene dichloride. There was 0.0004 moles of dinonylnaphthalene sulfonic acid as the extractant in the phase.

The phases were shaken together for two minutes, separated, and the pH value of the aqueous and the amount of valine left was measured. The following data, including concentration ratios of valine in the organic layer to valine in the aqueous layer was found:

| Extractant: | Dinonylnaphthalene sulfonic acid in ethylene dichloride | |
|---|---|---|
| pH value | [Valine in Organic] / [Valine in Aqueous] | Percent Valine Extracted |
| 1.85 | 2.7 | 73 |
| 1.38 | 2.0 | 67 |
| 1.06 | 1.1 | 52 |
| 0.75 | 0.83 | 46 |
| 0.43 | 0.65 | 39 |
| 0.12 | 0.38 | 27 |

EXAMPLE III

Ten extractions of valine were completed at different pH values. The aqueous phase in each case contained 0.0005 moles of valine, and was 15 ml in volume. HCl was used to adjust the acid pH values, and NaOH was used for basic values.

The organic phase solvent was ethylene dichloride, and the extractant was ALIQUAT ® 336 (previously described in Example I), which was present in an amount of 0.001 moles in each organic phase for each extraction completed at each of the ten pH values. The organic phase was 10 ml in volume, and after being shaken together with the aqueous phase, it was separated. The concentration of valine in the aqueous phase was then analyzed, and the phase pH measured.

The data is shown in the following chart, which includes the concentration ratio of: valine in the organic layer to valine in the aqueous layer, and the present valine extracted for each pH value are:

| pH value | [Valine in Organic] / [Valine in Aqueous] | Percent Valine Extracted |
|---|---|---|
| 13.28 | 0.14 | 12 |
| 12.98 | 0.14 | 12 |
| 12.59 | 0.27 | 21 |
| 10.05 | 0.18 | 15 |
| 9.44 | 0.14 | 12 |
| 4.36 | 0.00 | 0 |
| 3.00 | 0.03 | 3 |
| 1.82 | 0.00 | 0 |
| 0.89 | 0.03 | 3 |
| 0.16 | 0.10 | 9 |

EXAMPLE IV

Extraction procedure: a known amount of tryptophan, in a 15 ml volume of water was shaken in a separation funnel with a known amount of extractant in an organic solvent for two minutes. The phases were separated, and the pH value of the aqueous phase was measured along with the amount of amino acid in the phase.

The experiment was comparative, showing the extraction of tryptophan using two different organic solvents. Two series of extractions (Series A and Series B) were similar using identical procedures except for the solvent.

Series A

Ethylene dichloride was the solvent.

Each aqueous phase was: 15 ml in volume; 0.0005 moles of tryptophan; acid pH values achieved with HCl; basic pH values achieved with NaOH.

The extractant was ALIQUAT ® 336 (previously described in Example I).

The organic phases were 10 ml in volume, had 0.001 moles of ALIQUAT ® 336 in the ethylene dichloride solvent.

The following data was recorded:

| pH value | [Conc. of Tryptophan in the Organic Phase] / [Conc. of Tryptophan in the Aqueous Phase] | Percent Tryptophan Extracted |
|---|---|---|
| 13.35 | 1.1 | 52 |
| 12.95 | 1.4 | 58 |
| 10.26 | 0.50 | 33 |
| 2.23 | 0.10 | 9 |
| 1.99 | 0.03 | 3 |
| 1.97 | 0.00 | 0 |
| 1.43 | 0.18 | 15 |
| 1.21 | 0.06 | 6 |
| 0.18 | 0.10 | 9 |

Series B

Solvent: Decahydronaphthalene

Each aqueous phase was: 15 ml in volume, had 0.0005 moles of tryptophan, acid pH values achieved with HCl, and NaOH used for basic pH values.

Each organic phase was 10 ml and had 0.001 moles of ALIQUAT ® 336 (previously described in Example I) which was the extractant used in the decahydronaphthalene solvent.

The following data was recorded:

| pH value | [Conc. of Tryptophan in the Organic Phase] / [Conc. of Tryptophan in the Aqueous Phase] | Percent Tryptophan Extracted |
|---|---|---|
| 13.42 | 4.5 | 82 |
| 12.94 | 4.5 | 82 |
| 10.02 | 3.125 | 42 |
| 2.23 | 0.00 | 0 |
| 2.10 | 0.00 | 0 |
| 1.60 | 0.00 | 0 |
| 1.32 | 0.179 | 15 |
| 1.13 | 0.031 | 3 |
| 0.74 | 0.065 | 6 |
| 0.11 | 0.737 | 42 |

A 500 ml solution of ethylene dichloride and 0.055 moles of dinonylnaphthalene sulfonic acid was added to a 1 liter flask equipped with mechanical stirrer, Dewar condenser, gas inlet and a thermometer and heated to about 68C until dissolved. 0.05 Moles of phenylalanine was added and the mixture was stirred. Hydrogen chloride gas was introduced into the solution, and a precipitate formed. After 15 to 20 minutes the escaping gas formed a dense white cloud and the reaction was considered to be completed. The precipitate was collected, washed, and dried. Upon analysis it was found that the precipitate was phenylalanine hydrochloride. This demonstrates that where the extractant is anionic, a hydrogenhalide can be used to precipitate the amino acids in order to recover the amino acid from an organic phase.

EXAMPLE VI 0.3 Moles (70.3 grams) of valine and approximately 25 grams (g) of NaOH were made to 2 liters at a pH of 11.98. The extractant for the organic phase was the previously described ALIQUAT® 336. 100 g of ALIQUAT® 336 was made to one liter with ethylene dichloride. The ALIQUAT® 336 solution was contacted with 500 ml of the aqueous valine solution, and the aqueous phase discarded. This was repeated three times with fresh 500 ml portions of the aqueous valine solution. 500 ml of the resulting organic solution (to be used as the organic phase) was drained into a three-necked 1 liter flask equipped with a mechanical stirrer, Dewar condenser, gas inlet, and a thermometer. The contents of the flask were heated to 30° C., and HCl gas was introduced for 35 minutes until large amounts of this gas began to collect in the condenser. The gas was then turned off and precipitate collected, dried for two hours in a vacuum oven, and analyzed. The precipitate was found to be valine hydrochloride.

EXAMPLE VII

The other 500 ml quantity of the organic phase ( as prepared in Examples VI containing valine and the quaternary ammonium salt) was placed in a three-necked 1 liter flask equipped with mechanical stirrer, Dewar condenser, gas inlet and a thermometer. The contents of the flask were again heated to 30C, and gaseous ammonia was bubbled through the solution. No precipitate formed, showing that gaseous ammonia was incapable of removing the valine from the organic. This indicates that where a cationic extractant is used, stripping of the amino acid can not be achieved with a similar (cationic) base.

EXAMPLE VIII

An ethylene dichloride solution was prepared which was 0.1 molar in phenylalanine, and 0.11 molar in dinonylnaphthalene sulfonic acid by heating the mixture to 70° C. in a three-necked 1 liter flask which was equipped with a mechanical stirrer, Dewar condenser, gas inlet, and a thermometer. Gaseous ammonia was bubbled through the solution while it was maintained at a temperature of 70° C. A solid product formed while the NH$_3$ was added over about 20 minutes, after which time the gas was turned off; and the precipitate collected, filtered, dried and analyzed. The precipitate was found to be phenylalanine. This demonstrates that amino acids can be removed from organic solutions having anionic extractants by using gaseous ammonia to form a solid precipitate.

Having thus described our invention, we claim:

1. A process for the extraction of an amino acid from an aqueous solution thereof in which said amino acid is not present in its zwitterionic form, said amino acid being selected from the group consisting of isoleucine, leucine, lysine, methionine, beta-alanine, phenylalanine, threonine, tryptophan, valine, tyrosine, glutamic acid and aspartic acid, comprising (a) contacting said aqueous solution containing said aqueous solution with a solution of a water insoluble extractant in a water immiscible organic solvent which forms a separate organic phase from said aqueous solution, said contact taking place for a sufficient length of time to allow the amino acid to be extracted from said aqueous phase into said organic phase, said water insoluble extractant being an organic sulfonic acid selected from the group consisting or organic sulfonic acids having the formula:

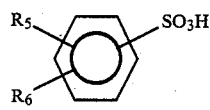

where R$_5$ and R$_6$ are aliphatic hydrocarbon groups individually with from about 6 to about 22 carbon atoms, where R$_5$ and R$_6$ together contain at least 18 carbon atoms, and where neither R$_5$ and R$_6$ are smaller than a C$_6$; and organic sulfonic acids having the structural formula:

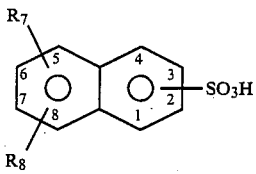

where R$_7$ and R$_8$ are aliphatic hydrocarbon groups containing from about 4 to about 22 carbon atoms, where R$_7$, R$_8$, or the sulfonic group may be attached to positions 1–8 on the aromatic rings, and where neither R$_7$ nor R$_8$ is smaller than a C$_4$, and where R$_7$ and R$_8$ together have at least 18 carbon atoms, (b) separating said organic phase containing said amino acid from said aqueous phase,
    (c) removing said amino acid from said organic phase now containing said amino acid by contacting said organic phase with an aqueous acidic solution or a gas selected from the group consisting of NH$_3$, HCl, HBr, Co$_2$ and SO$_2$.

2. A process as defined in claim 1 wherein said amino acid is stripped from said organic phase upon contact with said aqueous acidic solution forming an aqueous stripping phase now containing said amino acid and separating said organic phase from said aqueous stripping phase.

3. A process as described in claim 2 wherein the aqueous stripping phase is acidified with an acid selected from the group consisting of: phosphoric, nitric, sulfuric, hydrochloric, hydrofluoric, and hydrobromic.

4. A process as described in claim 1 wherein there is from about 0.25 moles of extractant in the organic solution per mole of amino acid in the aqueous mixture, to about 10 moles of extractant in organic solution per mole of amino acid in the aqueous mixture.

5. A process as described in claim 1 wherein, after separation from the aqueous mixture, said amino acids, present in the organic phase are precipitated by contacting the organic solution with a gas selected from the group consisting of: NH$_3$, HCl, HBr, CO$_2$ and SO$_2$.

6. A process as described in Claim 1 wherein the amino acid is phenylalanine.

7. A process as defined in claim 1 wherein the aqueous stripping phase is maintained at a pH of less than 0.5 or greater than 2.5 when contacting the organic phase.

8. A process as described in claim 7 wherein the aqueous stripping phase while contacting the organic phase is maintained at a pH greater than 2.5 by using a base selected from the group consisting of ammonium hydroxide, potassium hydroxide, sodium hydroxide or sodium carbonate.

* * * * *